United States Patent [19]

Nakaoji

[11] 4,297,520

[45] Oct. 27, 1981

[54] PROCESS FOR PREPARING ANISALDEHYDE

[75] Inventor: Kozo Nakaoji, Osaka, Japan

[73] Assignee: Daiwa Chemical Company Ltd., Japan

[21] Appl. No.: 127,071

[22] Filed: Mar. 4, 1980

[30] Foreign Application Priority Data

Mar. 12, 1979 [JP] Japan .................................. 54-29067

[51] Int. Cl.³ .............................................. C07C 45/28
[52] U.S. Cl. .................................... 568/426; 568/442; 204/89
[58] Field of Search ................................ 568/426, 442

[56] References Cited

U.S. PATENT DOCUMENTS 2,794,813  6/1957  Farinacci ........................ 568/426 X 3,985,809  10/1976  Becking .............................. 568/426

FOREIGN PATENT DOCUMENTS 2252318  6/1975  France .

OTHER PUBLICATIONS

Wiberg, Oxidation in Organic Chemistry, Part A (1965) 96–105.

Primary Examiner—Bernard Helfin
Attorney, Agent, or Firm—Larson and Taylor

[57] ABSTRACT p-Methoxytoluene is oxidized with a dichromate ion forming substance and sulfuric acid to give anisaldehyde in good yields. The oxidation proceeds with improved efficiency in the presence of a manganese compound.

9 Claims, No Drawings

PROCESS FOR PREPARING ANISALDEHYDE

This invention relates to a process for preparing anisaldehyde.

Various processes have already been reported for producing anisaldehyde. For example, it is known to produce the compound by oxidizing p-methyoxytoluene with manganic sulfate serving as an oxidizing agent and prepared from potassium permanganate and manganous sulfate. According to another known process, anisaldehyde is produced by oxidizing p-methoxytoluene with manganic sulfate prepared by the electrolysis of manganous sulfate, and the manganous sulfate resulting from the oxidizing step is electrolyzed again to manganic sulfate for repeated use. With the former process, the use of expensive potassium permangante as the oxidizing agent renders the product costly, and it is impossible to effect more than 40% conversion of the starting material (p-methoxytoluene) since a higher degree of conversion will lead to lower anisaldehyde selectivity. The latter process involves a great difference in optimum sulfuric acid concentration between the step of regnerating manganous sulfate to manganic sulfate by electrolysis (at a sulfuric acid concentration of at least about 30%) and the step of oxidizing p-methoxytoluene to anisaldehyde with the regenerated manganic sulfate (at a sulfuric acid concentration of about 5%), so that the solution resulting from the electrolytic regeneration step is not usable as it is for the oxidation of p-methoxytoluene but requires a cumbersome procedure, such as concentration or salting out as by the addition of ammonium sulfate, for the recovery of manganic sulfate. Accordingly the process, when practiced on an industrial scale, involves considerable complexity and consumption of energy for the second step as well as for the first step of electrolyzing manganous sulfate, consequently rendering anisaldehyde costly to manufacture. The process is therefore not as commercially valuable as is expected. Like the former process, this process is unable to achieve higher degrees of conversion in excess of 40%.

An object of this invention is to provide a process for preparing anisaldehyde with use of inexpensive oxidizing agents with a high degree of conversion and with high selectivity.

Another object of the invention is to provide a process for preparing anisaldehyde in which the waste liquid resulting from an oxidation step is electrolyzed for regeneration to give an aqueous solution which is usable as it is as an oxidizing solution.

Still another object of the invention is to provide a process for preparing anisaldehyde at a reduced cost without causing pollution.

These and other objects of the invention will become apparent from the following description.

The present invention provides a process for preparing anisaldehyde characterized by oxidizing p-methoxytoluene with a dichromate ion forming substance and sulfuric acid, electrolytically oxidizing the aqueous waste solution resulting from the oxidation step to obtain a regenerated solution containing a dichromate ion forming substance and sulfuric acid, and repeatedly using the regenerated solution as it is as an oxidizing agent.

I have also found that when p-methoxytoluene is oxidized to anisaldehyde by the above process in the presence of a manganese compound, it is possible to inhibit the formation of by-products, such as anisic acid, tar or like resinous substance, etc., in the reaction system. Useful manganese compounds are those capable of releasing manganese ions in the reaction system, namely, in an aqueous solution of sulfuric acid and chromic sulfate. They include inorganic salts and organic salts of manganese, such as manganous sulfate, manganic sulfate, manganous chloride, manganic chloride, manganous nitrate, manganic nitrate, manganous acetate, manganic acetate, etc. Such a manganese compound, once admixed with the reaction system, is usable in circulation.

A description will now be given of the reaction conditions for practicing the present invention, such as the amount of dichromate ion forming substance relative to p-methoxytoluene, concentration of sulfuric acid, concentration of manganese compound, reaction temperature, amount of reaction solution, reaction time, etc.

Useful dichromate ion forming substances are those convertable to dichromate ions in the presence of sulfuric acid, namely, under an acid condition. Examples of such substances are chromic anhydride ($CrO_3$), dichromic acid, and Na, K, $NH_4$ and like salts of the acid. The dichromate ion forming substance is used in an amount of up to 100 parts by weight, usually about 30 to about 95 parts by weight, preferably 50 to 90 parts by weight, calculated as $CrO_3$ per 100 parts by weight of the starting material, i.e., p-methoxytoluene. Sulfuric acid is used in such an amount that the reaction system usually has a sulfuric acid concentration of about 5 to about 40% by weight, preferably about 10 to about 30% by weight, more preferably about 15 to about 23% by weight. The manganese compound is used in such an amount that the reaction system contains about 0.1 to about 100 g/liter, preferably about 0.1 to 16 g/liter, more preferably about 1 to about 8 g/liter, of manganese. The reaction temperature, which is determined in accordance with the concentration of sulfuric acid, is usually about 10 to about 90° C., preferably about 75 to about 85° C.

The amount of the solution to be reacted with p-methoxytoluene, which also greatly influences the yield of anisaldehyde, is usually about 3 to 30 times, preferably about 8 to 12 times, the volume of p-methoxytoluene used. The reaction time is usually about 3 to about 6 hours.

The reaction is conducted by stirring in a suitable container p-methoxytoluene and a solution of dichromate ion forming substance and sulfuric acid, with or without a manganese compound contained in the solution. Anisaldehyde can be prepared with ease according to the invention when the amounts of dichromate ion forming substance, sulfuric acid, manganese compound and reaction solution, and other conditions are suitably determined. The reaction mixture resulting from the oxidation step is placed into a suitable container, allowed to stand for some time and then separated into an organic and an aqueous layer. When desired, a suitable amount of extractant, such as toluene or methyl ethyl ketone, is added to the aqueous layer, and the mixture is shaken or stirred to extract small amounts of remaining p-methoxytoluene and anisaldehyde. The extract is combind with the organic layer. The organic layer, with or without the extact combined therewith, is then distilled to the fractions of the extractant, unreacted p-methoxytoluene and anisaldehyde.

To prepare the desired product more advantageously according to the invention, the aqueous waste solution resulting from the oxidation step and containing chromic sulfate and sulfuric acid, with or without the manganese compound further contained therein, is electrolytically oxidized to obtain a regenerated solution, which is repeatedly used as an oxidizing solution. This step can be practiced, for example, by electrolyzing the waste solution with use of lead anode and cathode, whereby a solution is obtained which contains dichromate ion forming substance and sulfuric acid for reuse. The electrolysis is conducted, for example, at a current density of about 1 to about 4 A/dm$^2$ to electrolyze the chromium compounds in the waste solution to an extent corresponding to about 80 to about 90% of the total amount of chromium. The concentration of chromium compounds in the solution, which influences the electrolysis efficiency, is preferably about 15 to about 100 g/liter, more preferably about 45 to about 60 g/liter, calculated as chromium. In view of the electrolysis efficiency, therefore, it is especially desirable that the oxidizing solution for oxidizing p-methoxytoluene to anisaldehyde contain the chromium compounds in an amount of about 45 to about 60 g/liter calculated as chromium as will be shown in Example 3. It is also desired that part of the solution resulting from the oxidation step be used as it is for reaction with the starting material and that the remaining portion be electrolyzed to a regenerated oxidizing solution. To avoid variations in the sulfuric acid concentration and chromium concentration of the solution to be electrolyzed, it is also desirable to use the waste solution as the cathode solution and the cathode solution of the previous electrolysis step as the anode solution.

Given below are examples of this invention.

EXAMPLE 1

Water (940 ml) is placed into a 2-liter, 3-necked flask equipped with a stirrer, thermometer, reflux condenser and placed in a water bath, and 54 g of chromic anhydride is dissolved in the water with stirring. To the solution is added 174 g of sulfuric acid. The mixture is adjusted to 35° C., and 100 g of p-methoxytoluene is added thereto. The mixture is heated to a progressively increasing temperature with stirring and maintained at 40° to 45° C. The initial reddish brown color of the mixture changes gradually to dark green and finally to green. The reaction is completed in about 3 hours. The reaction mixture is placed into a separating funnel, allowed to stand for some time and thereafter separated into organic and aqueous layers. The aqueous layer is extracted twice with a 80 ml portion of toluene each time. The extract is combined with the organic layer, and the combined mixture is dehydrated after removing the remaining small amount of chromic sulfate. The mixture is then distilled to fractions.

At first, toluene is distilled off at a reduced pressure of 165 mm Hg. Then, the vacuum is gradually increased to 5 mm Hg. The unreacted p-methoxytoluene is distilled at 40° to 47° C. Further distillation gives 24 g of anisaldehyde at 70° to 85° C. as a light yellow, viscous liquid. The amount of recovered p-methoxytoluene is 65 g.

EXAMPLE 2

Into the same flask as in Example 1 are placed 400 ml of water, 86 g of sulfuric acid and 100 g of p-methoxytoluene, and the mixture is stirred. A 540 ml quantity of water, 54 g of chromic anhydride and 200 g of sulfuric acid are placed in a 1-liter beaker to prepare an oxidizing solution. The solution is slowly added dropwise to the mixture in the flask with stirring while maintaining the reaction temperature constantly at 35° C. After the whole solution has been added, the mixture is stirred for further 20 minutes. The total reaction time is 5 hours and a half. The reaction mixture is treated and distilled to fractions in the same manner as in Example 1, giving 32 g of anisaldehyde and 60 g of recovered unreacted p-methoxytoluene.

EXAMPLE 3

Electrolysis is conducted at an electric current density of 3 A/dm$^2$ for 29 hours in an electrolysis bath equipped with a diaphragm, using as each of anodic and cathodic solutions 1 liter of a solution containing 225 g/liter of chromic sulfate and 200 g/liter of sulfuric acid and resulting from an oxidation process such as those given in Examples 1 and 2. Analysis of the resulting anodic solution shows that the solution contains 49 g/liter of chromic sulfate, 90 g/liter of chromic anhydride and 355 g/liter of sulfuric acid. The electrolysis efficiency is 82%. Into the same flask as used in Example 1 is placed 400 ml of a solution obtained from the previous oxidation, and 100 g of p-methoxytoluene is added thereto. The mixture is stirred. To the mixture is slowly added 600 ml of the above anodic solution from a dropping funnel over a period of 3$\frac{1}{3}$ hours while maintaining the reaction temperature at 40° C. The reaction mixture is stirred for further 10 minutes. The mixture is treated in the same manner as in Example 1, giving 30 g of anisaldehyde and 60 g of recovered unreacted p-methoxytoluene. The aqueous solution separated from the organic layer is divided into a 40% portion which is subsequently used to repeat the oxidation process and a 60% portion which is regenerated as an oxidizing solution by electrolysis.

In the same manner as the above procedure, the oxidation and electrolysis processes are repeated 5 times. The results are shown in Table 1 below.

TABLE 1

| Times | p-Methoxy toluene Used (g) | p-Methoxy toluene Recovered (g) | Reaction temp. (°C.) | Reaction time (hrs.) | Yield of anisaldehyde (g) | Yield of anisaldehyde (%) | Electrolysis efficiency (%) |
|---|---|---|---|---|---|---|---|
| 1st | 100 | 60 | 40 | 3$\frac{1}{2}$ | 30 | 67.5 | 82 |
| 2nd | 100 | 63 | 40 | 3$\frac{2}{3}$ | 29 | 70.6 | 80 |
| 3rd | 100 | 63 | 40 | 3$\frac{2}{3}$ | 28 | 68.1 | 81 |
| 4th | 100 | 62 | 40 | 3$\frac{1}{2}$ | 29 | 68.7 | 80 |
| 5th | 100 | 63 | 40 | 3$\frac{1}{2}$ | 28 | 68.1 | 79.5 |

EXAMPLE 4

Electrolysis is carried out in the same manner as Example 3 with the use of a solution containing 305 g/liter of chromic sulfate and 205 g/liter of sulfuric acid obtained from a previous oxidation process. The resulting anodic solution is found to contain 43 g/liter of chromic sulfate, 133 g/liter of chromic anhydride and 400 g/liter of sulfuric acid. The same oxidation process as in Example 3 is conducted with the use of the above anodic solution except that the reaction is carried out at 80° C. for 2$\frac{1}{3}$ hours, giving 60 g of anisaldehyde and 23 g of recovered unreacted p-methoxytoluene. Conversion 77%. Yield 70%. Aldehyde selectivity 74%.

EXAMPLE 5

Into the same flask as in Example 1 are placed 400 ml of water, 87 g of sulfuric acid, 5 g of manganic sulfate and 100 g of p-methoxytoluene, and the mixture is stirred. Into a 1-liter beaker are placed 540 ml of water, 86 g of chromic anhydride and 246 g of sulfuric acid to prepare an oxidizing solution. The oxidation process of Example 2 is repeated in the same manner except that the reaction temperature is maintained at 80° C for 2⅓ hours. The reaction mixture is treated in the same manner as in Example 1, affording 70 g of anisaldehyde, 27 g of unreacted p-methoxytoluene and 5 g of the residue. Conversion 73%. Yield 86%. Aldehyde selectivity 80%.

EXAMPLE 6

Electrolysis is conducted at an electric current density of 3 A/dm$^2$ for 34 hours in an electrolysis bath equipped with a diaphragm, using as each of anodic and cathodic solutions 1 liter of a solution containing 243 g/liter of chromic sulfate, 204 g/liter of sulfuric acid and 6 g/liter of manganic sulfate and resulting from an oxidation process such as those given in Examples 1 and 2. Analysis of the resulting anodic solution shows that the solution contains 43 g/liter of chromic sulfate, 102 g/liter of chromic anhydride, 354 g/liter of sulfuric acid and 5.5 g/liter of manganic sulfate. The electrolysis efficiency is 80%. Into the same flask as used in Example 1 is placed 400 ml of a solution obtained from the previous oxidation, and 70 g of p-methoxytoluene is added thereto. The mixture is heated at 80° C. with stirred. To the mixture is slowly added 588 ml of the above anodic solution from a dropping funnel over a period of 2 hours while maintaining the reaction temperature at 80° to 81° C. The reaction mixture is stirred for further 20 minutes. The mixture is treated in the same manner as in Example 1, giving 50 g of anisaldehyde, 20 g of recovered unreacted p-methoxytoluene and 3 g of residue. The aqueous solution separated from the organic layer is divided into a 40% portion which is subsequently used to repeat the oxidation process and a 60% portion which is regenerated as an oxidizing solution by electrolysis.

In the same manner as the above procedure, the oxidation and electrolysis processes are repeated 3 times. The results are shown in Table 2 below.

TABLE 2

| Times | p-Methoxytoluene Used (g) | p-Methoxytoluene Recovered (g) | Reaction temp. (°C.) | Reaction time (hrs.) | Conversion (%) | Anisaldehyde Yield (g) | Anisaldehyde Yield (%) | Selectivity (%) | Electrolysis efficiency (%) |
|---|---|---|---|---|---|---|---|---|---|
| 1st | 70 | 19 | 80–81 | 2⅓ | 72.9 | 51 | 89.7 | 83.3 | 81 |
| 2nd | 70 | 20 | 80–81 | 2⅓ | 71.4 | 49 | 87.9 | 80.0 | 80 |
| 3rd | 70 | 19 | 80–81 | 2⅓ | 72.9 | 50 | 87.9 | 81.6 | 80.5 |

I claim:

1. A process for preparing anisaldehyde comprising oxidizing p-methoxytoluene with a dichromate ion forming substance in an amount of 30 to 100 parts by weight calculated as CrO$_3$ per 100 parts by weight of p-methoxytoluene and sulfuric acid in a concentration of about 5 to 40% by weight, to provide an aqueous phase and an organic phase, separating said phases and recovering anisaldehyde and p-methoxytoluene from said organic phase.

2. A process as defined in claim 1 wherein the aqueous waste solution resulting from the oxidation step is electrolytically oxidized to obtain a regenerated solution containing a dichromate ion forming substance and sulfuric acid, and the regenerated solution is repeatedly used as it is as an oxidizing agent.

3. A process as defined in claim 1 wherein the oxidation by said dichromate ion forming substance and said sulfuric acid is conducted in the presence of a manganese compound in a concentration of about 0.1 to about 100 grams/liter calculated as manganese.

4. A process as defined in claim 2 wherein the aqueous waste solution includes a manganese compound in a concentration of about 0.1 to about 100 grams/liter calculated as manganese.

5. A process as defined in claim 3 wherein the manganese compound is manganous sulfate, manganic sulfate, manganous chloride, manganic chloride, manganous nitrate, manganic nitrate, manganous acetate or manganic acetate.

6. A process as defined in any one of claims 1 to 4 wherein the reaction temperature of the oxidation step is about 10° to 90° C.

7. A process as defined in claim 6 wherein the reaction temperature of the oxidation step is about 75° to about 85° C.

8. A process as defined in claim 2 or 4 wherein the electrolysis is conducted at a current density of about 1 to about 4 A/dm$^2$.

9. A process as defined in claim 2 or 4 wherein the solution to be subjected to electrolysis has a chromium concentration of about 15 to about 100 g/liter.

* * * * *